(12) United States Patent
Takeda et al.

(10) Patent No.: US 10,772,984 B2
(45) Date of Patent: Sep. 15, 2020

(54) ELASTIC POROUS FILM AND ARTICLE

(71) Applicant: NITTO DENKO CORPORATION, Osaka (JP)

(72) Inventors: Yasuhiro Takeda, Matsuyama (JP); Yoshitake Shigematsu, Matsuyama (JP); Kohei Takeda, Ibaraki (JP); Shou Uchida, Ibaraki (JP); Muneshige Nakagawa, Ibaraki (JP); Shinsuke Ikishima, Ibaraki (JP)

(73) Assignee: NITTO DENKO CORPORATION, Osaka (JP)

( * ) Notice: Subject to any disclaimer, the term of this patent is extended or adjusted under 35 U.S.C. 154(b) by 224 days.

(21) Appl. No.: 15/564,090

(22) PCT Filed: Apr. 12, 2016

(86) PCT No.: PCT/JP2016/061787
§ 371 (c)(1),
(2) Date: Oct. 3, 2017

(87) PCT Pub. No.: WO2016/167241
PCT Pub. Date: Oct. 20, 2016

(65) Prior Publication Data
US 2018/0133951 A1    May 17, 2018

(30) Foreign Application Priority Data

Apr. 15, 2015 (JP) .................. 2015-082962
Nov. 30, 2015 (JP) .................. 2015-232629

(51) Int. Cl.
*B29D 7/01* (2006.01)
*C08K 13/04* (2006.01)
(Continued)

(52) U.S. Cl.
CPC ........ *A61L 15/24* (2013.01); *A61F 13/00012* (2013.01); *A61F 13/15203* (2013.01);
(Continued)

(58) Field of Classification Search
CPC ........ A61L 15/24; A61L 15/225; A61L 15/18; A61L 15/20; A61L 15/42; B29C 55/10;
(Continued)

(56) References Cited

U.S. PATENT DOCUMENTS 4,472,328 A    9/1984  Sugimoto et al.
4,613,643 A    9/1986  Nakamura et al.
(Continued)

FOREIGN PATENT DOCUMENTS

CN    1312319    9/2001
CN    1839042    9/2006
(Continued)

OTHER PUBLICATIONS

Buschow, K. H. J. (2001). Encyclopedia of materials: Science and technology. Amsterdam: Elsevier. p. 7705-7708 (Year: 2001).*
(Continued)

*Primary Examiner* — Michael Zhang
(74) *Attorney, Agent, or Firm* — Greenblum & Bernstein, P.L.C.

(57) ABSTRACT

The stretchable porous film of the present invention includes voids in a surface thereof, in which: the stretchable porous film has an air permeability measured with an Oken-type air permeability meter of less than 99,999 sec/100 cc; the stretchable porous film has such an extending direction that an air permeability measured with the Oken-type air permeability meter in a state in which the stretchable porous film is extended by 100% becomes less than 60,000 sec/100 cc; and the stretchable porous film has such a pulling direction that when, in a hysteresis test, the stretchable
(Continued)

porous film is pulled from a width of 20 mm and an inter-chuck distance of 30 mm to an inter-chuck distance of 60 mm at a pulling speed of 50 mm/min and held for 1 minute, and then the pulling of the inter-chuck distance is released, a residual strain becomes 10 mm or less.

17 Claims, 3 Drawing Sheets

(51) Int. Cl.
| | |
|---|---|
| B29C 55/10 | (2006.01) |
| A61F 13/15 | (2006.01) |
| A61F 13/49 | (2006.01) |
| A61L 15/22 | (2006.01) |
| C08L 23/12 | (2006.01) |
| B29K 23/00 | (2006.01) |
| B29L 31/48 | (2006.01) |
| B29K 105/16 | (2006.01) |
| A61L 15/24 | (2006.01) |
| A61L 15/18 | (2006.01) |
| C08J 9/00 | (2006.01) |
| C08K 3/26 | (2006.01) |
| C08L 23/04 | (2006.01) |
| B32B 27/32 | (2006.01) |
| A61F 13/00 | (2006.01) |
| B29C 55/00 | (2006.01) |
| A61F 13/514 | (2006.01) |
| B29C 55/04 | (2006.01) |
| A61F 13/511 | (2006.01) |
| C08J 5/18 | (2006.01) |
| A61L 15/20 | (2006.01) |
| A61L 15/42 | (2006.01) |
| C08L 23/14 | (2006.01) |
| B32B 27/08 | (2006.01) |
| B32B 27/30 | (2006.01) |
| B32B 27/20 | (2006.01) |
| B32B 27/36 | (2006.01) |
| B32B 3/26 | (2006.01) |

(52) U.S. Cl.
 CPC .. *A61F 13/49009* (2013.01); *A61F 13/51121* (2013.01); *A61F 13/51401* (2013.01); *A61L 15/18* (2013.01); *A61L 15/20* (2013.01); *A61L 15/225* (2013.01); *A61L 15/42* (2013.01); *B29C 55/005* (2013.01); *B29C 55/04* (2013.01); *B29C 55/10* (2013.01); *B29D 7/01* (2013.01); *B32B 3/266* (2013.01); *B32B 27/08* (2013.01); *B32B 27/20* (2013.01); *B32B 27/205* (2013.01); *B32B 27/306* (2013.01); *B32B 27/308* (2013.01); *B32B 27/32* (2013.01); *B32B 27/327* (2013.01); *B32B 27/36* (2013.01); *C08J 5/18* (2013.01); *C08J 9/00* (2013.01); *C08K 3/26* (2013.01); *C08K 13/04* (2013.01); *C08L 23/04* (2013.01); *C08L 23/12* (2013.01); *C08L 23/14* (2013.01); *A61F 2013/15552* (2013.01); *B29K 2023/00* (2013.01); *B29K 2105/16* (2013.01); *B29K 2995/0065* (2013.01); *B29L 2031/4835* (2013.01); *B29L 2031/4878* (2013.01); *B32B 2250/03* (2013.01); *B32B 2250/40* (2013.01); *B32B 2264/025* (2013.01); *B32B 2264/0235* (2013.01); *B32B 2264/102* (2013.01); *B32B 2264/104* (2013.01); *B32B 2270/00* (2013.01); *B32B 2307/50* (2013.01); *B32B 2307/724* (2013.01); *B32B 2555/02* (2013.01); *C08J 2323/12* (2013.01); *C08J 2423/16* (2013.01); *C08K 2003/265* (2013.01); *C08K 2201/003* (2013.01); *C08K 2201/005* (2013.01); *C08L 2203/02* (2013.01); *C08L 2203/16* (2013.01); *C08L 2205/025* (2013.01)

(58) Field of Classification Search
 CPC . B29C 55/005; B29C 55/04; A61F 13/15203; A61F 13/49009; A61F 2013/15552; A61F 13/51401; A61F 13/51121; A61F 13/00012; C08L 23/12; C08L 23/04; C08L 23/14; C08L 2203/02; C08L 2203/16; C08L 2205/025; C08J 9/00; C08J 2323/12; C08J 2423/16; C08J 5/18; C08K 3/26; C08K 2003/265; C08K 2201/003; C08K 2201/005; C08K 13/04; B29D 7/01; B32B 2250/03; B32B 2250/40; B32B 2264/0235; B32B 2264/025; B32B 2264/102; B32B 2264/104; B32B 2270/00; B32B 2307/50; B32B 2307/724; B32B 2555/02; B32B 27/20; B32B 27/205; B32B 27/306; B32B 27/308; B32B 27/327; B32B 27/36; B32B 27/32; B32B 3/266; B29K 2023/00; B29K 2105/16; B29K 2995/0065; B29L 2031/4835; B29L 2031/4878
 See application file for complete search history.

(56) References Cited

U.S. PATENT DOCUMENTS

| | | | |
|---|---|---|---|
| 4,921,652 | A | 5/1990 | Tsuji et al. |
| 5,001,205 | A | 3/1991 | Hoel |
| 5,185,035 | A | 2/1993 | Brown et al. |
| 5,385,972 | A | 1/1995 | Yamamoto et al. |
| 5,501,679 | A | 3/1996 | Krueger et al. |
| 5,691,034 | A | 11/1997 | Krueger et al. |
| 6,322,883 | B1 | 11/2001 | Williams |
| 6,472,445 | B1 | 10/2002 | Takahashi et al. |
| 6,514,606 | B2 | 2/2003 | Kinoshita et al. |
| 6,703,439 | B2 | 3/2004 | Yano et al. |
| 7,220,478 | B2 | 5/2007 | McCormack et al. |
| 7,270,723 | B2 | 9/2007 | McCormack et al. |
| 7,279,723 | B2 | 10/2007 | Matsumura et al. |
| 2001/0018465 | A1 | 8/2001 | Yano et al. |
| 2002/0064651 | A1 | 5/2002 | Kinoshita et al. |
| 2004/0170852 | A1* | 9/2004 | Gustafson ............... B32B 5/18 428/500 |
| 2005/0043460 | A1 | 2/2005 | McCormack et al. |
| 2005/0101206 | A1 | 5/2005 | McCormack et al. |
| 2006/0024520 | A1 | 2/2006 | Kong et al. |
| 2009/0258210 | A1 | 10/2009 | Iyad et al. |
| 2016/0159031 | A1 | 6/2016 | Ikishima et al. |
| 2016/0200078 | A1 | 7/2016 | Arakawa |
| 2018/0133357 | A1* | 5/2018 | Takeda ................... B29C 55/10 |

FOREIGN PATENT DOCUMENTS

| | | | | |
|---|---|---|---|---|
| EP | 0993832 | A1 * | 4/2000 | ......... A61F 13/5146 |
| EP | 1250225 | | 8/2005 | |
| EP | 1656246 | | 5/2006 | |
| EP | 3023247 | A1 | 5/2016 | |
| EP | 3045311 | A1 | 7/2016 | |
| JP | S58-15538 | | 1/1983 | |
| JP | S60-166436 | | 8/1985 | |
| JP | S62-148537 | | 7/1987 | |
| JP | H05-050522 | | 3/1993 | |
| JP | H05-501386 | | 3/1993 | |
| JP | 5-310980 | A | 11/1993 | |
| JP | H07-286051 | | 10/1995 | |
| JP | H08-053561 | | 2/1996 | |
| JP | H10-139953 | | 5/1998 | |
| JP | H11-048410 | | 2/1999 | |

(56) References Cited

FOREIGN PATENT DOCUMENTS

| JP | H11-151782 | | 6/1999 |
|---|---|---|---|
| JP | H11-240984 | A | 9/1999 |
| JP | H11-245338 | | 9/1999 |
| JP | H11-291404 | | 10/1999 |
| JP | 2000-001557 | | 1/2000 |
| JP | 2000-167037 | A | 6/2000 |
| JP | 2002-146070 | | 5/2002 |
| JP | 3308025 | | 5/2002 |
| JP | 2002-307627 | | 10/2002 |
| JP | 2002-316359 | A | 10/2002 |
| JP | 2008-169304 | | 7/2006 |
| JP | 2008-088293 | | 4/2008 |
| JP | 2008-179757 | A | 8/2008 |
| JP | 2009-114434 | | 5/2009 |
| JP | 2009-126000 | | 6/2009 |
| JP | 2010-065088 | A | 3/2011 |
| JP | 2012-177106 | A | 9/2012 |
| JP | 2013-040261 | | 2/2013 |
| JP | 2015-20317 | | 2/2015 |
| JP | 2015-021105 | | 2/2015 |
| JP | 2015-063633 | | 4/2015 |
| JP | 2015-86367 | | 5/2015 |
| WO | 01/47710 | | 7/2001 |
| WO | 01/47710 | A1 | 7/2001 |
| WO | 2005/023544 | | 3/2005 |
| WO | 2015/008595 | | 1/2015 |
| WO | 2015/037507 | | 3/2015 |
| WO | 2016/167242 | | 10/2016 |

OTHER PUBLICATIONS

Supplementary European Search Report dated Jan. 28, 2019 in European Application No. 16780033.
International Search Report from Application No. PCT/JP2016/061787, dated Jul. 19, 2016.
International Preliminary Report on Patentability from Application No. PCT/JP2016/061787, dated Oct. 17, 2017.
Office Action dated Dec. 10, 2019 in Chinese Application No. 201680021971.1 with English translation.
Office Action dated Nov. 20, 2019 in Chinese Application No. 201680021935.5 with English translation.
International Search Report from Application No. PCT/JP2016/061788, dated Jun. 21, 2016 with English translation.
International Preliminary Report on Patentability from Application No. PCT/JP2016/061788, dated Oct. 17, 2017 with English translation.
Ueda—JP H07-286051 A—MT—Expansible sheet—ISR D6—1995 (Year: 1995)—English abstract.
Toda—JP H11-151782 A—MT—stretchable composite film—ISR D1—1999 (Year: 1999)—English abstract.
Toda—JP 2008-169304 A—MT—resin for stretch film—2008 (Year: 2008)—English abstract.
Series_ TAFMER™, a high performance elastome—Mitsui Chemicals (Year: 2018).
Ueda—JP H07-286051 A—Expansible sheet—ISR D6—1995—Human translation (Year: 1995).
Office Action issued in Japanese Patent Application No. 2016-056671, dated Sep. 24, 2019, with English translation.
Office Action issued in JP Patent Application No. 2015-232629, dated Sep. 24, 2019, with English translation.
Office Action dated Dec. 4, 2018 in U.S. Appl. No. 15/564,302.
Final Office Action dated May 22, 2019 in U.S. Appl. No. 15/564,302.
Office Action dated Jan. 30, 2020 in U.S. Appl. No. 15/564,302.
Collette, Macromolecules 1989, 22, 3851-3858.
ExxonMobil—Vistamaxx 6202 datasheet—2017 (Year: 2017).
ExxonMobil—Vistamaxx 6102 datasheet—B—Jan. 2017 (Year: 2017).
Third Party Observation dated Jul. 30, 2019 filed in Japanese patent application No. 2015-232629, with English translation.
The Micropedia of the Britannica International Encyclopedia, "permanent set", downloaded Jul. 10, 2019, https://kotobank.jp/word/%E%BC%B0%B8%E4B9%85%E3%81%B2%E3%81%9A%E3%81%BF-35835 with English translation.
The Micropedia of the Britannica International Encyclopedia, "elongation percentage", downloaded Jul. 10, 2019, https://kotobank.jp/word/%E6%B0%E4%B95581%B3%E7%8E%87-112372) with English translation.
"Basic Physical Properties of Tafmer DF & A Brands", download undated, https://www.mitsuichem.com/sites/default/files/media/document/2018/brand001_2.pdf with English Translation.
Elastomers Division, Mobility Business Sector, Mitsui Chemicals, Inc., "Product Introduction of Tafmer", downloaded undated (indicates Aug. 24, 2018 document), https://www.chem-t.com/fax/images/tmp_file4_1535093776.pdf) with English translation.
Plastics Today, "Exxon's Singapore expansion on schedule; Vistamaxx broadened", downloaded Jul. 11, 2019 (indicates Apr. 27, 2010 document), https://www.plasticstoday.com/content/exxon-s-singapore-expansion-on-schedule-vistamaxx-broadened/10727890114121.
ExxonMobil Japan G.K., Propylene-based Elastomer "Vistamaxx Series", downloaded Jul. 11, 2019, https://www.ipros.jp/product/detail/print?objectId=1504356&hub=45+goggle with English translation.
Junichi Imuta, "Synthesis of Elastomers by Metallocene Catalysts", download undated, https://www.jstage.jst.go.jp/article/kobunshi1952/46/11/46_11_824/_pdf with English translation.
Glossary of Technical Terms in Manufacturing Industry, "Melt Flow Rate", downloaded Jul. 22, 2019,https://www.ipros.jp/monosiri/term/%E3%83%A1%E3%83%AB%E3%83%88%E3%83%95%E3%83%AD%E3%83%BC%E3%83%AC%E3%83%BC%E3%83%88 with English translation.
Office Action dated Jun. 10, 2020 in U.S. Appl. No. 15/564,302.
Mitsui Chemicals—TAFMER A grades_a—2011 (Year:2011).
Office Action dated Mar. 30, 2020 in European Application No. 16780033.3.
Office Action dated May 26, 2020 in Japanese Application No. 2016-056671 with English translation.
Yutaka Kikuchi et al., Structure and Properties of Thermoplastic Elastomer, Journal of the Society of Rubber Science and Technology, Japan, 1991, vol. 64, No. 9, pp. 38-44, "Development and Perspective of Elastomer Engineering" with English translation.

* cited by examiner

ELASTIC POROUS FILM AND ARTICLE

TECHNICAL FIELD

The present invention relates to a stretchable porous film and an article.

BACKGROUND ART

Various stretchable films are adopted for stretchable articles such as sanitary articles, for example, a sticking plaster.

Such stretchable film is required to have not only excellent stretchability but also excellent air permeability in some applications. For example, a conventional and typical sticking plaster (see, for example, Patent Literature 1) has some degree of waterproof property because polyvinyl chloride is used as the polymer component of the stretchable film of the sticking plaster. However, the sticking plaster has poor air permeability, and hence involves a problem in that a maceration phenomenon in which during the bonding of the sticking plaster to a skin, the skin of a portion having bonded thereto the sticking plaster becomes stuffy to whiten occurs.

CITATION LIST

Patent Literature

[PTL 1] JP 2000-167037 A

SUMMARY OF INVENTION

Technical Problem

The present invention has been made to solve the conventional problems, and an object of the present invention is to provide a stretchable porous film having excellent stretchability and excellent air permeability. Another object of the present invention is to provide an article including such stretchable porous film.

Solution to Problem

A stretchable porous film according to one embodiment of the present invention includes voids in a surface thereof, in which:

the stretchable porous film has an air permeability measured with an Oken-type air permeability meter of less than 99,999 sec/100 cc;

the stretchable porous film has such an extending direction that an air permeability measured with the Oken-type air permeability meter in a state in which the stretchable porous film is extended by 100% becomes less than 60,000 sec/100 cc; and the stretchable porous film has such a pulling direction that when, in a hysteresis test, the stretchable porous film is pulled from a width of 20 mm and an inter-chuck distance of 30 mm to an inter-chuck distance of 60 mm at a pulling speed of 50 mm/min and held for 1 minute, and then the pulling of the inter-chuck distance is released, a residual strain becomes 10 mm or less.

In one embodiment, the air permeability measured with the Oken-type air permeability meter is less than 60,000 sec/100 cc.

In one embodiment, the air permeability measured with the Oken-type air permeability meter is less than 40,000 sec/100 cc.

In one embodiment, the air permeability measured with the Oken-type air permeability meter in a state in which the stretchable porous film is extended by 100% is less than 30,000 sec/100 cc.

In one embodiment, the air permeability measured with the Oken-type air permeability meter in a state in which the stretchable porous film is extended by 100% is less than 5,000 sec/100 cc.

In one embodiment, the residual strain is from 8 mm to 1 mm.

In one embodiment, the residual strain is from 6 mm to 2 mm.

In one embodiment, the stretchable porous film of the present invention has a thickness of from 30 μm to 300 μm.

In one embodiment, the stretchable porous film of the present invention has a thickness of from 50 μm to 150 μm.

In one embodiment, the stretchable porous film of the present invention includes a polymer component and a filler.

In one embodiment, the polymer component contains a propylene-based elastomer.

In one embodiment, a content of the propylene-based elastomer in the polymer component is from 30 wt % to 100 wt %.

In one embodiment, the propylene-based elastomer has a MFR of from 0.1 g/10 min to 18 g/10 min.

In one embodiment, the propylene-based elastomer has a MFR of from 2 g/10 min to 5 g/10 min.

In one embodiment, the propylene-based elastomer includes a metallocene-based elastomer.

In one embodiment, the polymer component contains linear low-density polyethylene.

In one embodiment, a content of the linear low-density polyethylene in the polymer component is from 5 wt % to 60 wt %.

In one embodiment, the filler includes at least one kind selected from inorganic particles and organic particles.

An article according to one embodiment of the present invention includes the stretchable porous film of the present invention.

In one embodiment, the article of the present invention further includes a pressure-sensitive adhesive layer.

Advantageous Effects of Invention

According to the present invention, the stretchable porous film having excellent stretchability and excellent air permeability can be provided. The article including such stretchable porous film can also be provided.

DESCRIPTION OF EMBODIMENTS

«Stretchable Porous Film»

A stretchable porous film of the present invention is a stretchable porous film including voids in its surface. The stretchable porous film of the present invention has excellent air permeability because the stretchable porous film includes the voids in its surface.

The air permeability of the stretchable porous film of the present invention measured with an Oken-type air permeability meter is less than 99,999 sec/100 cc, preferably less than 80,000 sec/100 cc, more preferably less than 70,000 sec/100 cc, still more preferably less than 60,000 sec/100 cc, particularly preferably less than 50,000 sec/100 cc, most preferably less than 40,000 sec/100 cc. When the air permeability of the stretchable porous film of the present invention measured with the Oken-type air permeability meter falls within the range, the stretchable porous film of the present invention can have excellent air permeability.

The stretchable porous film of the present invention has such an extending direction that an air permeability measured with the Oken-type air permeability meter in a state in which the stretchable porous film is extended by 100% becomes less than 60,000 sec/100 cc. The air permeability is preferably less than 50,000 sec/100 cc, more preferably less than 40,000 sec/100 cc, still more preferably less than 30,000 sec/100 cc, particularly preferably less than 10,000 sec/100 cc, most preferably less than 5,000 sec/100 cc. When the stretchable porous film of the present invention has such an extending direction that the air permeability measured with the Oken-type air permeability meter in a state in which the stretchable porous film is extended by 100% falls within the range, the stretchable porous film of the present invention can have excellent air permeability in its extended state.

The phrase "has an extending direction" means that the stretchable porous film of the present invention only needs to have at least one extending direction in which the air permeability falls within the range. When the stretchable porous film of the present invention is an unstretched film, a preferred example of such extending direction is typically every direction of the film, and when the stretchable porous film of the present invention is a uniaxially stretched film, a preferred example thereof is a direction perpendicular to the direction of the stretching (a CD direction when the film is stretched in its lengthwise (MD) direction). In addition, when the stretchable porous film of the present invention is a biaxially stretched film, an extending direction in which the air permeability falls within the range is determined by various conditions, such as whether the stretching is simultaneous stretching or sequential stretching, and a difference in stretching ratio between two axes.

The stretchable porous film of the present invention has such a pulling direction that when, in a hysteresis test, the stretchable porous film is pulled from a width of 20 mm and an inter-chuck distance of 30 mm to an inter-chuck distance of 60 mm at a pulling speed of 50 mm/min and held for 1 minute, and then the pulling of the inter-chuck distance is released, a residual strain becomes 10 mm or less. The residual strain is preferably from 9 mm to 1 mm, more preferably from 8 mm to 1 mm, still more preferably from 7 mm to 1 mm, particularly preferably from 6 mm to 2 mm, most preferably from 5 mm to 3 mm. When the stretchable porous film of the present invention has such a pulling direction that the residual strain falls within the range, the stretchable porous film of the present invention can have excellent stretchability.

The phrase "has a pulling direction" means that the stretchable porous film of the present invention only needs to have at least one pulling direction in which the residual strain falls within the range. When the stretchable porous film of the present invention is an unstretched film, a preferred example of such pulling direction is typically every direction of the film, and when the stretchable porous film of the present invention is a uniaxially stretched film, a preferred example thereof is a direction perpendicular to the direction of the stretching (a CD direction when the film is stretched in its lengthwise (MD) direction). In addition, when the stretchable porous film of the present invention is a biaxially stretched film, a pulling direction in which the residual strain falls within the range is determined by various conditions, such as whether the stretching is simultaneous stretching or sequential stretching, and a difference in stretching ratio between two axes.

The thickness of the stretchable porous film of the present invention is preferably from 30 μm to 300 μm, more preferably from 40 μm to 200 μm, still more preferably from 50 μm to 150 μm, particularly preferably from 60 μm to 140 μm, most preferably from 70 μm to 120 μm. When the thickness of the stretchable porous film of the present invention falls within the range, the stretchable porous film of the present invention can have more excellent stretchability and more excellent air permeability.

The stretchable porous film of the present invention preferably includes a polymer component and a filler.

Figure 1:
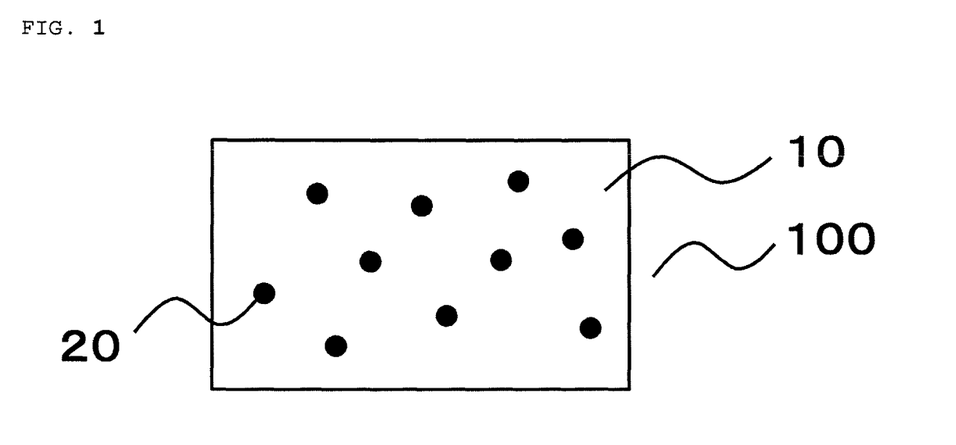
FIG. 1 is a schematic plan view of an example of a stretchable porous film according to one embodiment of the present invention.

FIG. 1 is a schematic plan view of an example of a stretchable porous film according to one embodiment of the present invention. In FIG. 1, a stretchable porous film 100 includes a polymer component 10 and a filler 20.

Figure 2:
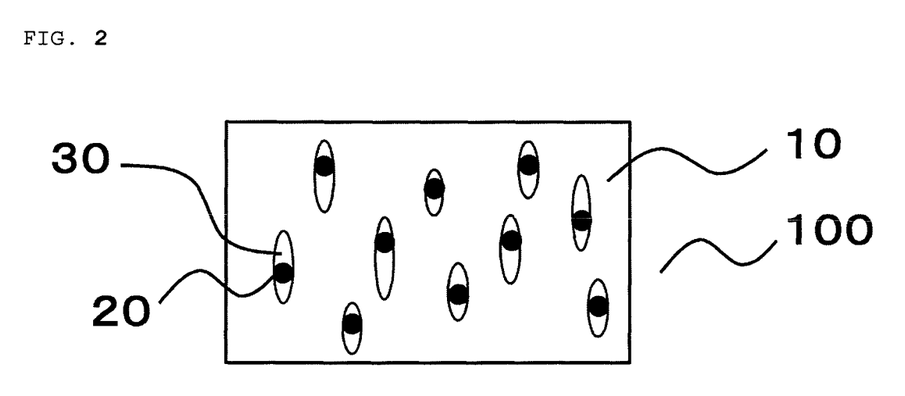
FIG. 2 is a schematic plan view of another example of the stretchable porous film according to one embodiment of the present invention.

FIG. 2 is a schematic plan view of another example of the stretchable porous film according to one embodiment of the present invention. In FIG. 2, the stretchable porous film 100 includes the polymer component 10 and the filler 20, and further includes voids 30.

When the stretchable porous film of the present invention is such embodiment as illustrated in FIG. 1, the stretchable porous film can be turned into such embodiment as illustrated in FIG. 2 by performing its extension. That is, when the stretchable porous film of the present invention is such embodiment as illustrated in FIG. 1, moderate voids can be produced in the surface of the stretchable porous film of the present invention by performing the extension. By virtue of the moderate voids, the stretchable porous film of the present invention can express sufficient air permeability. Further, the stretchable porous film can have a waterproof property as in a conventional and typical sticking plaster.

In the case where the stretchable porous film of the present invention is such embodiment as illustrated in FIG. 1, the stretchable porous film can express excellent air permeability even when not extended because an interface between the polymer component and the filler is present by virtue of the presence of the filler.

Such embodiment as illustrated in FIG. 1 or such embodiment as illustrated in FIG. 2 can be adopted as the stretchable porous film of the present invention in accordance with performance that a site where the stretchable porous film is used is required to have.

Any appropriate polymer component may be adopted as the polymer component in the stretchable porous film of the present invention to the extent that the effects of the present invention are not impaired.

The polymer component preferably contains a propylene-based elastomer.

When the polymer component contains the propylene-based elastomer, the stretchable porous film of the present invention can express more excellent stretchability. In addition, when the polymer component contains the propylene-based elastomer, the stretchable porous film of the present invention can express more excellent air permeability by being combined with the filler.

The propylene-based elastomers may be only one kind of elastomer, or may be two or more kinds of elastomers.

When the stretchable porous film of the present invention contains the propylene-based elastomer, its heat stability is improved, and hence, for example, heat decomposition at the time of the production of the stretchable porous film of the present invention can be suppressed. In addition, when the stretchable porous film of the present invention contains the propylene-based elastomer, its storage stability is improved, and hence fluctuations in physical property values during the storage of the stretchable porous film of the present invention can be suppressed.

When the stretchable porous film of the present invention contains the propylene-based elastomer, a production process for the stretchable porous film of the present invention can be simplified, and hence its processing cost can be suppressed. This is because of the following reason: when the propylene-based elastomer is adopted, extrusion molding can be performed at the time of the production of the stretchable porous film of the present invention, and hence the need for the production of a master batch can be eliminated.

The content of the propylene-based elastomer in the polymer component is preferably from 30 wt % to 100 wt %, more preferably from 40 wt % to 95 wt %, still more preferably from 50 wt % to 90 wt %, particularly preferably from 55 wt % to 85 wt %, most preferably from 60 wt % to 80 wt % because the effects of the present invention are further expressed. When the content of the propylene-based elastomer in the polymer component is set within the range, the stretchable porous film of the present invention can express more excellent stretchability. In addition, when the content of the propylene-based elastomer in the polymer component is set within the range, the stretchable porous film of the present invention can express more excellent air permeability by being combined with the filler.

Examples of the propylene-based elastomer include a propylene copolymer, a propylene olefin block copolymer, a propylene olefin random copolymer, a propylene ethylene olefin block copolymer, and amorphous polypropylene.

The propylene-based elastomer has a density of preferably from 0.890 g/cm$^3$ to 0.830 g/cm$^3$, more preferably from 0.888 g/cm$^3$ to 0.835 g/cm$^3$, still more preferably from 0.886 g/cm$^3$ to 0.835 g/cm$^3$, particularly preferably from 0.885 g/cm$^3$ to 0.840 g/cm$^3$, most preferably from 0.885 g/cm$^3$ to 0.845 g/cm$^3$. When the density of the propylene-based elastomer is set within the range, the stretchable porous film of the present invention can express more excellent stretchability. In addition, when the density of the propylene-based elastomer is set within the range, the stretchable porous film of the present invention can express more excellent air permeability by being combined with the filler.

The propylene-based elastomer has a MFR at 230° C. and 2.16 kgf of preferably from 0.1 g/10 min to 18 g/10 min, more preferably from 0.5 g/10 min to 15 g/10 min, still more preferably from 1.0 g/10 min to 10 g/10 min, particularly preferably from 1.5 g/10 min to 7 g/10 min, most preferably from 2 g/10 min to 5 g/10 min. When the MFR of the propylene-based elastomer is set within the range, the stretchable porous film of the present invention can express more excellent stretchability. In addition, when the MFR of the propylene-based elastomer is set within the range, the stretchable porous film of the present invention can express more excellent air permeability by being combined with the filler.

The propylene-based elastomer is also available as a commercial product. Examples of such commercial product include some products in the "Tafmer" (trademark) series manufactured by Mitsui Chemicals, Inc., and some products in the "Vistamaxx" (trademark) series (e.g., Vistamaxx 7010) manufactured by Exxon Mobil Corporation.

The propylene-based elastomer is preferably a metallocene-based elastomer (a propylene-based elastomer that is a metallocene-based elastomer is sometimes referred to as "metallocene polypropylene-based elastomer"). The metallocene-based elastomer is an elastomer produced by using a metallocene catalyst. When the metallocene-based elastomer is adopted as the propylene-based elastomer, the stretchable porous film of the present invention can express more excellent stretchability. In addition, when the metallocene-based elastomer is adopted as the propylene-based elastomer, the stretchable porous film of the present invention can express more excellent air permeability by being combined with the filler.

The polymer component preferably contains linear low-density polyethylene.

When the polymer component contains the propylene-based elastomer and the linear low-density polyethylene, the stretchable porous film of the present invention can express more excellent stretchability. In addition, when the polymer component contains the propylene-based elastomer and the linear low-density polyethylene, the stretchable porous film of the present invention can express more excellent air permeability by being combined with the filler.

The linear low-density polyethylene may be only one kind of polyethylene, or may be two or more kinds of polyethylenes.

When the stretchable porous film of the present invention contains the propylene-based elastomer and the linear low-density polyethylene, its heat stability is improved, and hence, for example, heat decomposition at the time of the production of the stretchable porous film of the present invention can be suppressed. In addition, when the stretchable porous film of the present invention contains the propylene-based elastomer and the linear low-density polyethylene, its storage stability is improved, and hence fluctuations in physical property values during the storage of the stretchable porous film of the present invention can be suppressed.

When the stretchable porous film of the present invention contains the propylene-based elastomer and the linear low-density polyethylene, a production process for the stretchable porous film of the present invention can be simplified, and hence its processing cost can be suppressed. This is because of the following reason: when the propylene-based elastomer and the linear low-density polyethylene are adopted, extrusion molding can be performed at the time of the production of the stretchable porous film of the present invention, and hence the need for the production of a master batch can be eliminated.

The content of the linear low-density polyethylene in the polymer component is preferably from 0 wt % to 70 wt %, more preferably from 5 wt % to 60 wt %, still more preferably from 10 wt % to 50 wt %, particularly preferably from 15 wt % to 45 wt %, most preferably from 20 wt % to 40 wt % because the effects of the present invention are further expressed. When the content of the linear low-density polyethylene in the polymer component is set within the range, the stretchable porous film of the present invention can express more excellent stretchability. In addition, when the content of the linear low-density polyethylene in the polymer component is set within the range, the stretchable porous film of the present invention can express more excellent air permeability by being combined with the filler.

The linear low-density polyethylene has a density of preferably from 0.910 g/cm³ to 0.940 g/cm³. When the density of the linear low-density polyethylene is set within the range, the stretchable porous film of the present invention can express more excellent stretchability. In addition, when the density of the linear low-density polyethylene is set within the range, the stretchable porous film of the present invention can express more excellent air permeability by being combined with the filler.

The linear low-density polyethylene has a MFR at 230° C. and 2.16 kgf of preferably from 1 g/10 min to 50 g/10 min. When the MFR of the linear low-density polyethylene is set within the range, the stretchable porous film of the present invention can express more excellent stretchability. In addition, when the MFR of the linear low-density polyethylene is set within the range, the stretchable porous film of the present invention can express more excellent air permeability by being combined with the filler.

The linear low-density polyethylene is also available as a commercial product. Examples of such commercial product include some products in the "ULTZEX" (trademark) series manufactured by Prime Polymer Co., Ltd.

The linear low-density polyethylene is preferably metallocene-based linear low-density polyethylene. The metallocene-based linear low-density polyethylene is linear low-density polyethylene produced by using a metallocene catalyst. When the metallocene-based linear low-density polyethylene is adopted as the linear low-density polyethylene, the stretchable porous film of the present invention can express more excellent stretchability. In addition, when the metallocene-based linear low-density polyethylene is adopted as the linear low-density polyethylene, the stretchable porous film of the present invention can express more excellent air permeability by being combined with the filler.

The stretchable porous film of the present invention preferably includes the filler. The filler is preferably at least one kind selected from inorganic particles and organic particles. The filler may be only one kind of filler, or may be two or more kinds of fillers. When the stretchable porous film of the present invention contains the filler, the stretchable porous film of the present invention can express more excellent air permeability.

Examples of the inorganic particles include talc, titanium oxide, calcium oxide, magnesium oxide, zinc oxide, calcium carbonate, silica, clay, mica, barium sulfate, whisker, and magnesium hydroxide.

Examples of the organic particles include acrylic beads, styrene beads, and silicone resin particles.

Any appropriate average particle diameter may be adopted as the average particle diameter of the filler to the extent that the effects of the present invention are not impaired. Such average particle diameter of the filler is preferably from 0.5 μm to 50 μm. The adjustment of the average particle diameter of the filler within the range enables the stretchable porous film of the present invention to express more excellent air permeability.

Any appropriate content may be adopted as the content of the filler to the extent that the effects of the present invention are not impaired. The content of such filler is preferably from 50 parts by weight to 400 parts by weight with respect to 100 parts by weight of the polymer component in the stretchable porous film. The adjustment of the content of the filler within the range enables the stretchable porous film of the present invention to express more excellent air permeability.

The filler may be coated with a releasing agent for preventing aggregation. Examples of such releasing agent include a fatty acid amide-based releasing agent, a silicone-based releasing agent, a fluorine-based releasing agent, and a long-chain alkyl-based releasing agent. Of those, a fatty acid amide-based releasing agent is preferred, and a saturated fatty acid bisamide is more preferred. Any appropriate usage amount may be adopted as the usage amount of the releasing agent.

The stretchable porous film of the present invention may contain any appropriate other component to the extent that the effects of the present invention are not impaired. The other component may be only one kind of component, or may be two or more kinds of components. Examples of such other component include a UV absorber, a heat stabilizer, a filler, a lubricant, a colorant (e.g., a dye), an antioxidant, an anti-build up agent, an antiblocking agent, a foaming agent, other polymers, a tackifier, a plasticizer, an antidegradant, an antistatic agent, and a light stabilizer. Those components may be used alone or in combination thereof.

Examples of the UV absorber include a benzotriazole-based compound, a benzophenone-based compound, and a benzoate-based compound. Any appropriate content may be adopted as the content of the UV absorber as long as the UV absorber does not bleed out at the time of the forming.

Examples of the heat stabilizer include a hindered amine-based compound, a phosphorus-based compound, and a cyanoacrylate-based compound. Any appropriate content may be adopted as the content of the heat stabilizer as long as the heat stabilizer does not bleed out at the time of the forming.

«Production of Stretchable Porous Film»

Any appropriate method may be adopted as a method of producing the stretchable porous film of the present invention to the extent that the effects of the present invention are not impaired.

A typical example of the method of producing the stretchable porous film of the present invention is a method involving molding materials for the stretchable porous film with a T-die molding machine to produce the stretchable porous film. For example, a rolled body of the stretchable porous film of the present invention can be produced by: extruding the materials for the stretchable porous film with the T-die molding machine from its T-die; and then winding the extruded materials in a roll shape. In addition to the T-die method involving using the T-die, an inflation method or the like can also be adopted.

The stretchable porous film of the present invention may be obtained by subjecting an unstretched film to a stretching treatment. Such stretching treatment of the unstretched film may be referred to as "pre-extension". When the stretchable porous film of the present invention is obtained by subjecting the unstretched film to the stretching treatment, the stretchable porous film can express more excellent stretchability. In addition, when the stretchable porous film of the present invention is obtained by subjecting the unstretched film to the stretching treatment, the stretchable porous film can further express excellent air permeability by being combined with the filler.

The pre-extension is pre-extension having the following meaning: the stretchable porous film of the present invention is extended in advance in consideration of the fact that the stretchable porous film is extended again (post-extension) in its final use.

The pre-extension is preferably performed after the stretchable porous film of the present invention has been produced and sufficiently solidified.

The pre-extension may be performed on the entirety of the original length or width in at least one direction, or may be performed on part of the original length or width. In addition, the pre-extension may be performed in any appropriate direction. The pre-extension is preferably performed on the original length or width in at least one direction.

The extension degree of the pre-extension is preferably 1.5 times or more and less than 2.5 times (typically 2.0 times), more preferably 2.5 times or more and less than 3.5 times (typically 3.0 times), still more preferably 3.5 times or more and less than 4.5 times (typically 4.0 times), particularly preferably 4.5 times or more and less than 5.5 times (typically 5.0 times). For example, 2.0-time pre-extension means that when the original length of the stretchable porous film is represented by L, the stretchable porous film is extended (sometimes referred to as "stretched") to have a length of 2 L. The stretchable porous film of the present invention can express more excellent stretchability by being pre-extended to such extension degree. In addition, when the stretchable porous film of the present invention is pre-extended to such extension degree, the stretchable porous film can express more excellent air permeability by being combined with the filler.

The pre-extension is preferably performed at a temperature less than the melting point of the polymer component. The stretchable porous film of the present invention can express more excellent stretchability by being pre-extended at such temperature. In addition, when the stretchable porous film of the present invention is pre-extended at such temperature, the stretchable porous film can express more excellent air permeability by being combined with the filler.

When the stretchable porous film of the present invention is preferably pre-extended as described above, the polymer component undergoes plastic deformation or is extended beyond the brittle fracture point of the polymer, and hence the stretchable porous film can express excellent stretchability.

«Application of Stretchable Porous Film»

The stretchable porous film of the present invention can be used in any appropriate article in which the effects of the present invention can be effectively utilized. That is, the article of the present invention includes the stretchable porous film of the present invention. A typical example of such article is a sticking plaster.

EXAMPLES

The present invention is hereinafter specifically described by way of Examples. However, the present invention is by no means limited to these Examples. Test and evaluation methods in Examples and the like are as described below. In addition, "part (s)" means "part(s) by weight" and "%" means "wt %" unless otherwise stated.

<Air Permeability>

An air permeability was measured with an Oken-type air permeability meter (sec/100 cc) (manufactured by Asahi Seiko Co., Ltd., product name: EG01-7-7MR). A stretchable porous film having an air permeability of more than 99,999 sec/100 cc was judged to have "no air permeability." The following two kinds of air permeability measurement were performed: the air permeability of a produced film in its present state (normal state) was measured; and the air permeability of the film in a state of being extended by 100% was measured. In the measurement in a state in which the produced film was extended by 100%, when the film was a uniaxially stretched film, the film was extended in a direction perpendicular to the direction of the stretching (a CD direction when the film was stretched in its lengthwise (MD) direction).

<Residual Strain>

Figure 3:
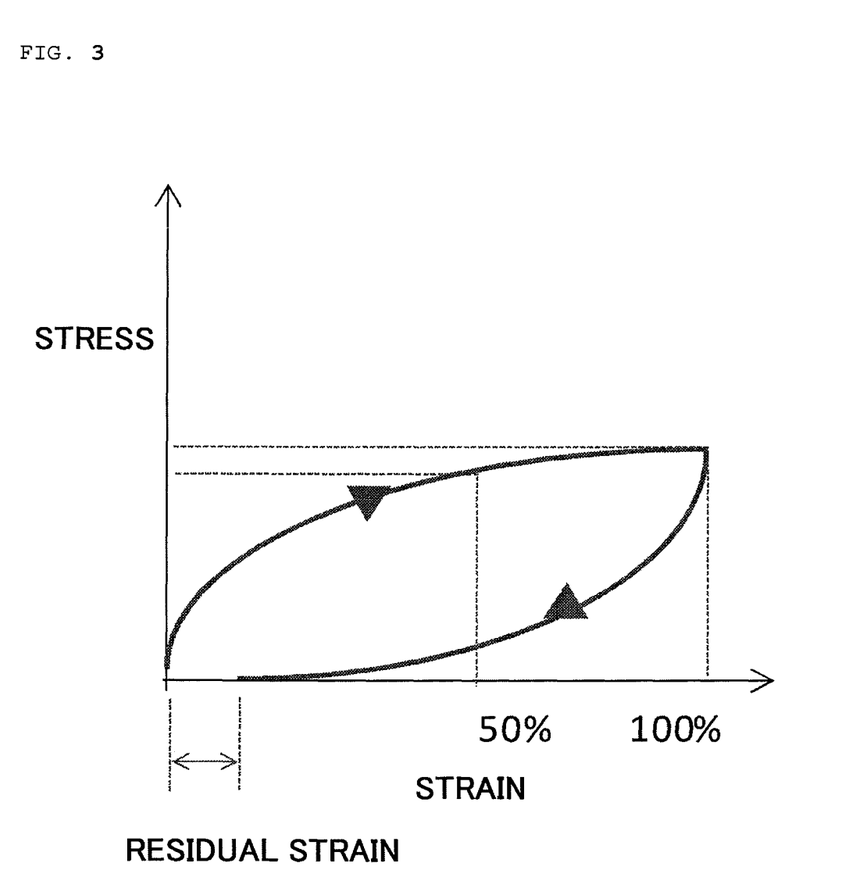
FIG. 3 is a graph for showing a relationship between a stress and a strain in a hysteresis test at the time of the measurement of a residual strain.

Such hysteresis test as shown in FIG. 3 was performed until a test piece having a width of 20 mm was pulled from an inter-chuck distance of 30 mm to an inter-chuck distance of 60 mm at a pulling speed of 50 mm/min and held for 1 minute, and then the pulling of the inter-chuck distance was released, followed by the measurement of a residual strain when the pulling of the inter-chuck distance was released. In the measurement of the residual strain, when a produced film was a uniaxially stretched film, the film was pulled in a direction perpendicular to the direction of the stretching (a CD direction when the film was stretched in its lengthwise (MD) direction).

<Evaluation of Maceration Phenomenon>

100 Parts of QUINTAC 3433N manufactured by Zeon Corporation, 50 parts of CLEARON M105 manufactured by Yasuhara Chemical Co., Ltd., and 150 parts of YS RESIN TO-L manufactured by Yasuhara Chemical Co., Ltd. were kneaded to prepare a hot-melt pressure-sensitive adhesive (A).

The hot-melt pressure-sensitive adhesive (A) was applied to one surface of a film to be evaluated by spraying. The film was cut into a piece measuring 80 mm in its CD direction by 20 mm in its lengthwise direction, and the piece was wound around a fingertip. The state of the skin of a portion having wound therearound the piece 24 hours after the winding was observed and evaluated by the following criteria.

A case in which the skin remains unchanged from its normal state: o

A case in which the skin whitens: x

<Test for Followability to Joint>

(Finger Joint)

The hot-melt pressure-sensitive adhesive (A) was applied to one surface of a film to be evaluated by spraying. The film was cut into a piece measuring 80 mm in its CD direction by 20 mm in its lengthwise direction, and the piece was wound around the second joint of a fingertip. A state after the joint had been bent for 5 minutes was observed and evaluated by the following criteria.

A case in which no gap is present between the finger and the film: o

A case in which the film completely extends, and hence a gap is present between the finger and the film: x (Elbow Joint)

The hot-melt pressure-sensitive adhesive (A) was applied to one surface of a film to be evaluated by spraying. The film was cut into a piece measuring 130 mm in its CD direction by 95 mm in its lengthwise direction, and the piece was wound around an elbow. A state after the elbow had been bent for 5 minutes was observed and evaluated by the following criteria.

A case in which no gap is present between the elbow and the film: o

A case in which the film completely extends, and hence a gap is present between the elbow and the film: x Example 1

140 Parts by weight of a metallocene polypropylene-based elastomer (manufactured by Exxon Mobil Corporation, product name: Vistamaxx 7010, density=0.861 g/cm$^3$, MFR=3 g/10 min), 200 parts by weight of calcium carbonate (average particle diameter=1.1 μm), 1 part by weight of stearic acid, and 1 part by weight of an antioxidant were melted and kneaded at 180° C. to provide a mixed material.

The resultant mixed material was loaded into an extruder, and was melted and extruded from its T-die. The extruded material was stretched in its lengthwise (MD) direction by a uniaxial roll stretching system at a stretching temperature of 60° C. and a stretching ratio of 4 times to provide a stretchable porous film (1) having a thickness of 100 μm.

The results are shown in Table 1.

Example 2

A stretchable porous film (2) having a thickness of 100 μm was obtained in the same manner as in Example 1 except that 98 parts by weight of the metallocene polypropylene-based elastomer (manufactured by Exxon Mobil Corporation, product name: Vistamaxx 7010, density=0.861 g/cm$^3$, MFR=3 g/10 min) and 42 parts by weight of linear low-density polyethylene (manufactured by Prime Polymer Co., Ltd., product name: ULTZEX 2022L, density=0.919 g/cm$^3$, MFR=2 g/10 min) were used instead of 140 parts by weight of the metallocene polypropylene-based elastomer (manufactured by Exxon Mobil Corporation, product name: Vistamaxx 7010, density=0.861 g/cm$^3$, MFR=3 g/10 min).

The results are shown in Table 1.

Example 3

A stretchable porous film (3) having a thickness of 100 μm was obtained in the same manner as in Example 1 except that 77 parts by weight of the metallocene polypropylene-based elastomer (manufactured by Exxon Mobil Corporation, product name: Vistamaxx 7010, density=0.861 g/cm$^3$, MFR=3 g/10 min) and 63 parts by weight of linear low-density polyethylene (manufactured by Prime Polymer Co., Ltd., product name: ULTZEX 2022L, density=0.919 g/cm$^3$, MFR=2 g/10 min) were used instead of 140 parts by weight of the metallocene polypropylene-based elastomer (manufactured by Exxon Mobil Corporation, product name: Vistamaxx 7010, density=0.861 g/cm$^3$, MFR=3 g/10 min).

The results are shown in Table 1.

Comparative Example 1

A stretchable porous film (C1) having a thickness of 100 μm was obtained in the same manner as in Example 1 except that 63 parts by weight of linear low-density polyethylene (manufactured by Prime Polymer Co., Ltd., product name: ULTZEX 2022L, density=0.919 g/cm$^3$, MFR=2 g/10 min) and 77 parts by weight of an ethylene-propylene terpolymer (manufactured by Mitsui Chemicals, Inc., product name: K-9720, MFR=2 g/10 min) were used instead of 140 parts by weight of the metallocene polypropylene-based elastomer (manufactured by Exxon Mobil Corporation, product name: Vistamaxx 7010, density=0.861 g/cm$^3$, MFR=3 g/10 min).

The results are shown in Table 2.

Comparative Example 2

A stretchable porous film (C2) having a thickness of 100 μm was obtained in the same manner as in Example 1 except that 63 parts by weight of linear low-density polyethylene (manufactured by Prime Polymer Co., Ltd., product name: ULTZEX 2022L, density=0.919 g/cm$^3$, MFR=2 g/10 min.) and 77 parts by weight of an α-olefin copolymer (manufactured by Mitsui Chemicals, Inc., product name: Tafmer PN-3560, MFR=6 g/10 min) were used instead of 140 parts by weight of the metallocene polypropylene-based elastomer (manufactured by Exxon Mobil Corporation, product name: Vistamaxx 7010, density=0.861 g/cm$^3$, MFR=3 g/10 min).

The results are shown in Table 2.

Comparative Example 3

A stretchable porous film (C3) having a thickness of 100 μm was obtained in the same manner as in Example 1 except that 98 parts by weight of a metallocene polypropylene-based elastomer (manufactured by Exxon Mobil Corporation, product name: Vistamaxx 6202, density=0.863 g/cm$^3$, MFR=20 g/10 min) and 42 parts by weight of linear low-density polyethylene (manufactured by Prime Polymer Co., Ltd., product name: ULTZEX 2022L, density=0.919 g/cm$^3$, MFR=2 g/10 min) were used instead of 140 parts by weight of the metallocene polypropylene-based elastomer (manufactured by Exxon Mobil Corporation, product name: Vistamaxx 7010, density=0.861 g/cm$^3$, MFR=3 g/10 min).

The results are shown in Table 2.

At the time of the production of the stretchable porous film (C3), the adhesion of the materials for the stretchable porous film to a roll was so strong that the production was not easy.

TABLE 1

|  |  | Example 1 | Example 2 | Example 3 |
|---|---|---|---|---|
| Vistamaxx 7010 | | 140 | 98 | 77 |
| Vistamaxx 6202 | | — | — | — |
| ULTZEX 2022L | | — | 42 | 63 |
| EPT K-9720 | | — | — | — |
| Tafmer PN-3560 | | — | — | — |
| Residual strain (mm) | | 3.0 | 3.3 | 5.4 |
| Air permeability (sec/100 cc) | Normal state | 30,923 | 11,487 | 6,892 |
| | 100% extended state | 3,369 | 1,807 | 263 |
| Maceration phenomenon | | ○ | ○ | ○ |
| Test for followability to joint | Finger | ○ | ○ | ○ |
| | Elbow | ○ | ○ | ○ |

TABLE 2

|  |  | Comparative Example 1 | Comparative Example 2 | Comparative Example 3 |
|---|---|---|---|---|
| Vistamaxx 7010 | | — | — | — |
| Vistamaxx 6202 | | — | — | 98 |
| ULTZEX 2022L | | 63 | 63 | 42 |
| EPT K-9720 | | 77 | — | — |
| Tafmer PN-3560 | | — | 77 | — |
| Residual strain (mm) | | 11.9 | 8.9 | 11.6 |
| Air permeability (sec/100 cc) | Normal state | 7,276 | 99,999 or more | 40,593 |
| | 100% extended state | 55 | 27,850 | 3,807 |
| Maceration phenomenon | | ○ | x | ○ |
| Test for followability to joint | Finger | x | ○ | x |
| | Elbow | x | ○ | x |

INDUSTRIAL APPLICABILITY

The stretchable porous film of the present invention can be used in any appropriate article in which the effects of the present invention can be effectively utilized. That is, the article of the present invention includes the stretchable porous film of the present invention. A typical example of such article is a sticking plaster.

REFERENCE SIGNS LIST

10 Polymer component
20 Filler
30 Void
100 Stretchable porous film

The invention claimed is:

1. A stretchable porous film, comprising voids in a surface thereof, wherein:
   the stretchable porous film includes a polymer component and a filler, the polymer component contains a propylene-based elastomer, and the propylene-based elastomer has a MFR of from 0.1 g/10 min to 18 g/10 min;
   the stretchable porous film has an air permeability measured with an Oken-type air permeability meter of less than 99,999 sec/100 cc;
   the stretchable porous film has such an extending direction that an air permeability measured with the Oken-type air permeability meter in a state in which the stretchable porous film is extended by 100% becomes less than 60,000 sec/100 cc; and
   the stretchable porous film has such a pulling direction that when, in a hysteresis test, the stretchable porous film is pulled from a width of 20 mm and an inter-chuck distance of 30 mm to an inter-chuck distance of 60 mm at a pulling speed of 50 mm/min and held for 1 minute, and then the pulling of the inter-chuck distance is released, a residual strain becomes 10 mm or less.

2. The stretchable porous film according to claim 1, wherein the air permeability measured with the Oken-type air permeability meter is less than 60,000 sec/100 cc.

3. The stretchable porous film according to claim 2, wherein the air permeability measured with the Oken-type air permeability meter is less than 40,000 sec/100 cc.

4. The stretchable porous film according to claim 1, wherein the air permeability measured with the Oken-type air permeability meter in a state in which the stretchable porous film is extended by 100% is less than 30,000 sec/100 cc.

5. The stretchable porous film according to claim 4, wherein the air permeability measured with the Oken-type air permeability meter in a state in which the stretchable porous film is extended by 100% is less than 5,000 sec/100 cc.

6. The stretchable porous film according to claim 1, wherein the residual strain is from 8 mm to 1 mm.

7. The stretchable porous film according to claim 6, wherein the residual strain is from 6 mm to 2 mm.

8. The stretchable porous film according to claim 1, wherein the stretchable porous film has a thickness of from 30 μm to 300 μm.

9. The stretchable porous film according to claim 8, wherein the stretchable porous film has a thickness of from 50 μm to 150 μm.

10. The stretchable porous film according to claim 1, wherein a content of the propylene-based elastomer in the polymer component is from 30 wt% to 100 wt%.

11. The stretchable porous film according to claim 1, wherein the propylene-based elastomer has a MFR of from 2 g/10 min to 5 g/10 min.

12. The stretchable porous film according to claim 1, wherein the propylene-based elastomer comprises a metallocene-based elastomer.

13. The stretchable porous film according to claim 1, wherein the polymer component contains linear low-density polyethylene.

14. The stretchable porous film according to claim 13, wherein a content of the linear low-density polyethylene in the polymer component is from 5 wt% to 60 wt%.

15. The stretchable porous film according to claim 1, wherein the filler comprises at least one kind selected from inorganic particles and organic particles.

16. An article, comprising the stretchable porous film of claim 1.

17. The article according to claim 16, further comprising a pressure-sensitive adhesive layer.

* * * * *